(12) United States Patent
Shackelford

(10) Patent No.: US 7,521,564 B1
(45) Date of Patent: Apr. 21, 2009

(54) HETEROCYCLIC SALTS OF HBS & HCS

(75) Inventor: Scott A. Shackelford, Lancaster, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 366 days.

(21) Appl. No.: 11/203,577

(22) Filed: Aug. 10, 2005

(51) Int. Cl.
  *C07D 233/02* (2006.01)
(52) U.S. Cl. .................... 548/300.1; 548/255; 548/250; 548/262
(58) Field of Classification Search ............. 548/300.1, 548/255, 250, 262
  See application file for complete search history.

(56) References Cited

U.S. PATENT DOCUMENTS 7,279,498 B2 * 10/2007 Keitz et al. .................. 514/400

* cited by examiner

*Primary Examiner*—Rei-tsang Shiao
(74) *Attorney, Agent, or Firm*—AFMCLO/JAZ; Thomas C. Stover

(57) ABSTRACT

The use of novel new heterocyclic borane and carborane salt ingredients for use as energetic, high density propellant fuels and fuel additives, or for gas generator and hydrogen storage applications. These subject and unique heterocyclic borane and carborane salts are comprised of both aromatic and non-aromatic heterocyclic cations with the necessary borane and/or carborane anions. Such salts with partially fluorinated borane or carborane anions would be candidate ingredients for metallized (e.g. boron, aluminum) propellant formulations. The high density provided by these unique heterocyclic borane and carborane compounds will be attractive for volume-limited propulsion systems.

5 Claims, No Drawings

HETEROCYCLIC SALTS OF HBS & HCS

STATEMENT OF GOVERNMENT INTEREST

The invention described herein may be manufactured and used by or for the Government for governmental purposes without the payment of any royalty thereon.

BACKGROUND OF THE INVENTION

The invention relates generally to high density propellant fuels, and more specifically, it relates to a new group of propellant fuels and fuel additives that use heterocyclic borane and carborane salt ingrediants.

Neutral borane and carborane compounds are known to be high energy compounds and have been considered for use in both formulated rocket propellant and explosives applications. Heterocyclic ionic solids and liquid salts, containing aromatic heterocyclic cations, are compounds that exhibit an almost non-existent vapor pressure and high ingredient densities.

Patented art of interest includes the following U.S. patents, the disclosures of which are incorporated herein by reference:

U.S. Pat. No. 4,855,508 entitled "Energetic diethers and process for their preparation" by Chapman, et al.

U.S. Pat. No. 4,424,398 entitled "Process for preparation of energetic plasticizers" by McGuire, et al.

U.S. Pat. No. 3,862,237 entitled "DIHYDROXY CARBORANES AND THE METHOD OF PREPARATION" by Knoeles.

U.S. Pat. No. 3,549,604 entitled "POLY-M-AND P-CARBORANYLENESULFIDES".

U.S. Pat. No. 3,531,443 entitled "POLY-m AND p-CARBORANYLENEDISULFIDES"

The Chapman patent describes a preparation of energetically substituted diether compounds as energetic curatives and plasticizers for rocket propellant binders as well as stable solid oxidizers and industrial explosives.

The McGuire patent describes a process for synthesizing energetic ethers, esters and acetals useful as plasticizers, monomers or prepolymers for propellant binder systems.

The Knowles patent describes a use of 1,7- and 1,12-dihydroxy meta- and paracarboranes are prepared by the controlled oxidation of the corresponding di(alkali metal) carborane salts, used as burn rate modifiers for propellants, as polymer intermediates, and also in boron-neutron capture therapy and neutron radiation shields.

In U.S. Pat. No. 3,549,604 polycarboranylenesulfides are prepared by reacting 1,12-bis(halosulfenyl)-p-carborane with the dilithio salt of p-carborane in an inert solvent.

In U.S. Pat. No. 3,531,443 polycarboranylene disulfides consisting essentially of recurring units of the formula: _ES_M_S3_ wherein M is the meta or para carboranylene radical, are prepared by reacting absolute ethanol with a bis(halosulfenyl)-m-carborane or a bis(halosulfenyl)-p-carborane. These polymeric products are useful as high energy fuels when compounded with oxidizers.

While the above-cited references are instructive, combining both fuel-like borane and carboranes as anionic species into a salt with heterocyclic cationic species should produce very low vapor pressure fuels with a resultant significant energy and/or density increase, as described below. Uniqueness in this present invention comes from the composition of these salts being comprised of heterocyclic cations with carborane and/or borane anions. Such salt compositions are unknown in the chemical literature. Additional invention novelty would come from their unprecedented use as potential propellant fuels, fuel additives, or in fuel cell, gas generator and hydrogen storage applications.

SUMMARY OF THE INVENTION

This invention disclosure concerns the use of novel new heterocyclic borane and carborane salt ingredients for use as energetic, high density propellant fuels and fuel additives, or for fuel cell, gas generator, and hydrogen storage applications. The subject heterocyclic borane and carborane salts are comprised of both aromatic and non-aromatic heterocyclic cations with the necessary accompanying borane and carborane anions. Specific heterocyclic salts containing selectively, partially fluorinated borane or carborane anions would be candidate ingredients for metallized (e.g. boron, aluminum) propellant formulations. The high density provided by these unique heterocyclic borane and carborane compounds will be attractive for volume-limited propulsion systems.

DESCRIPTION OF THE DRAWINGS

No Figures are used.

DETAILED DESCRIPTION OF THE PREFERRED EMBODIMENT

As mentioned above, this invention disclosure concerns the use of novel new heterocyclic borane and carborane salt ingredients for use as energetic, high density propellant fuels and fuel additives, or for gas generator and hydrogen storage applications. The subject heterocyclic borane and carborane salts are comprised of both aromatic and non-aromatic heterocyclic cations with the necessary accompanying borane and carborane anions.

Examples that reflect the chemical structures and types of heterocyclic borane and carborane compounds intended for the uses and applications outlined in this invention disclosure are provided below.

Main Synthesis Approach: The main synthesis approach for the subject compounds is conducted by the well-established metathesis reaction shown below. Some heterocyclic ring structures will be synthesized as necessary. Unless stated otherwise, R groups are H atoms or alkyl groups in chemical structure representations in this invention.

$$M^+(CB_{11}H_{12})^- +$$
$$M^+ = Cs^+, K^+, Ag^+, NR_4^+, \text{etc.};$$
$$Het^+X^- \longrightarrow$$
$$X^- = Cl^-, Br^-, I^-$$
$$Het^+(CB_{11}H_{12})^- + MX$$
$$Het^+ = \text{Heterocyclic Cation}$$

$K^\ominus$ [1-MeCB$_{11}$H$_{11}$]$^-$ (with CH$_3$ and C atom labeled) + H$_3$CN⊕NR Br$^\ominus$ ⟶

-continued

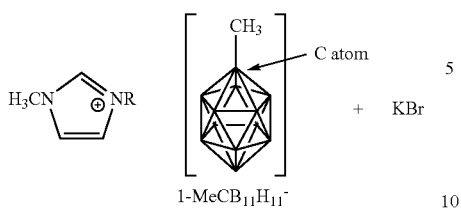

1-MeCB$_{11}$H$_{11}$⁻

I. New heterocyclic borane and carborane salt clusters using aromatic singularly-charged heterocyclic cations like, and derivatives of, those previously reported in the chemical literature (examples: imidazolium, 1,2,4-triazolium, 1,2,3-triazolium, and tetrazolium cations) are used.

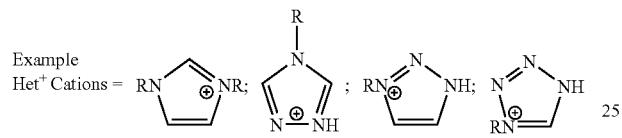

A. Heterocyclic Cations for Singularly-Charged Borane and Carborane (eg. borane cluster with one or more carbon atoms replacing a boron cluster atom) Salts (Two Structural Salt Examples):

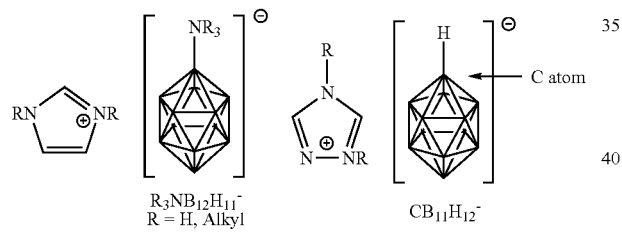

R$_3$NB$_{12}$H$_{11}$⁻
R = H, Alkyl

CB$_{11}$H$_{12}$⁻

B. Heterocyclic Cations for Multiply-Charged Borane (eg.: B$_{12}$H$_{12}$²⁻; B$_{10}$H$_{10}$²⁻; B$_6$H$_6$²⁻) Salts (Two Structural Examples):

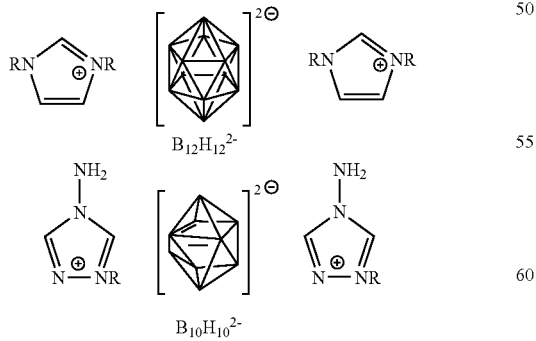

B$_{12}$H$_{12}$²⁻

B$_{10}$H$_{10}$²⁻

C. Multiply-Charged Borane Salts with Mixed Singularly-Charged Heterocyclic Cations (Two Structural Salt Examples):

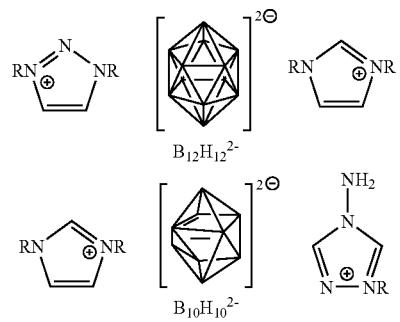

B$_{12}$H$_{12}$²⁻

B$_{10}$H$_{10}$²⁻

D. Heterocyclic Cations for Systematically Fluorinated Borane and Carborane Anions (Three Structural Salt Examples):

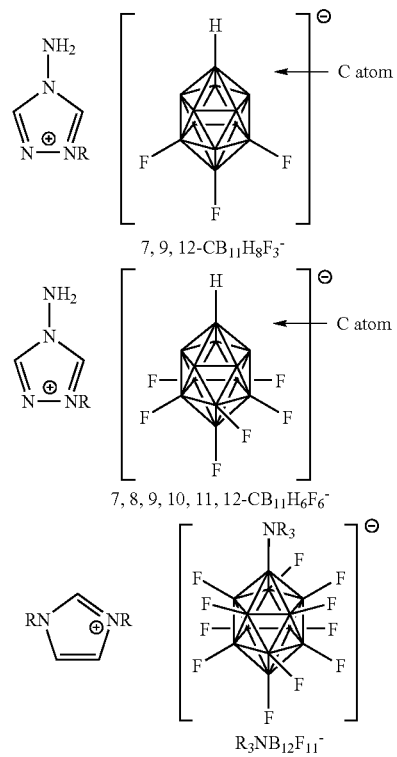

7, 9, 12-CB$_{11}$H$_8$F$_3$⁻

7, 8, 9, 10, 11, 12-CB$_{11}$H$_6$F$_6$⁻

R$_3$NB$_{12}$F$_{11}$⁻

F-CONTAINING CARBORANE ANIONS = 
CB$_{11}$H$_{12}$⊖ ; 12-CB$_{11}$H$_{11}$F$_1$⊖ ; 7, 12-CB$_{11}$H$_{10}$F$_2$⊖ ; 7, 9, 12-CB$_{11}$H$_9$F$_3$⊖ ; (no F-atoms)
7, 8, 10, 12-CB$_{11}$H$_8$F$_4$⊖ ; 7, 8, 9, 10, 11, 12-CB$_{11}$H$_6$F$_6$⊖ ; and CB$_{11}$HF$_{11}$⊖

F-CONTAINING BORANE ANION = R$_3$NB12F$_{11}$⊖

II. This also involves an incorporation of new aromatic and saturated heterocyclic cations with borane and carborane anions not previously reported in the chemical literature. This will include both unprecedented singularly- and multiply-charged cationic species.
A. New Aromatic Singularly-Charged Heterocyclic Cations for Borane and Carborane Salts (Two Structural Salt Examples):

SALTS OF:

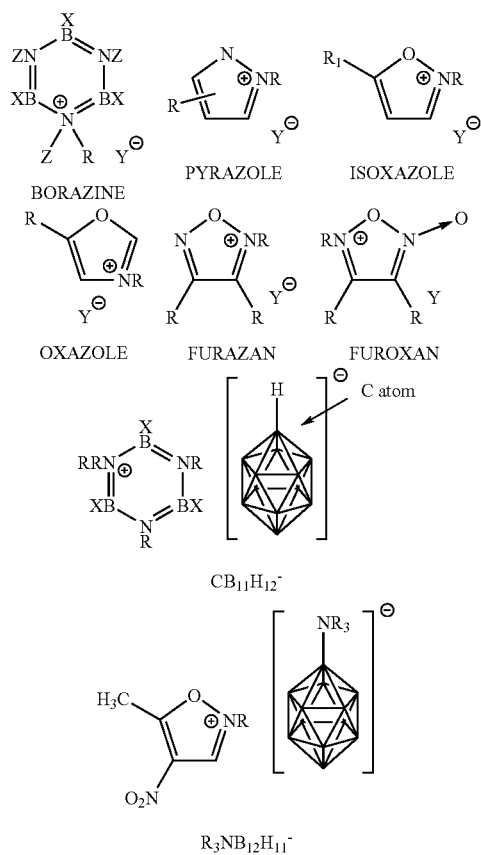

R = H, Alkyl

B. New Non-Aromatic Singularly-Charged Heterocyclic Cations for Borane and Carborane Salts (Two Structural Salt Examples):

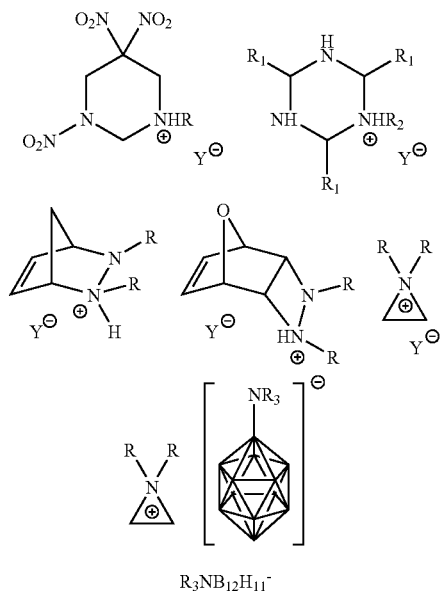

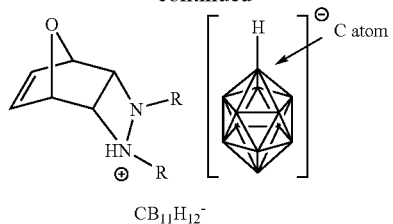

C. New Multiply-Charged Heterocyclic Cations for Singularly-Charged Borane and Carborane Salts (One Structural Salt Example):

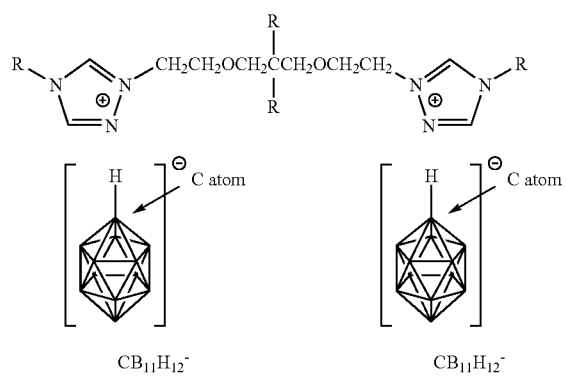

D. Multiply-Charged Heterocyclic Cations for Multiply-Charged Borane and Carborane Salts (One Structural Salt Example):

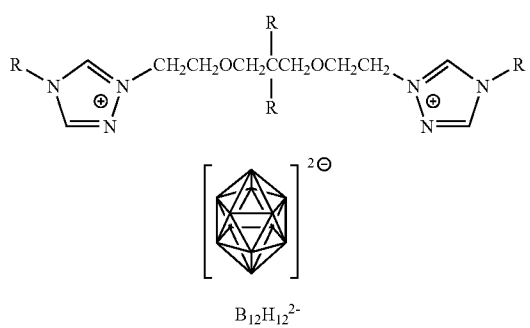

E. Multiply-Charged Heterocyclic Cations for Mixed Singularly-Charged Borane and Carborane Salts (One Structural Salt Example):

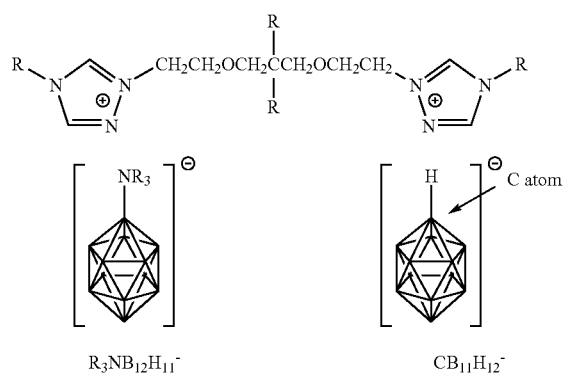

F. New Mixed Multiply-Charged Heterocyclic Cations for Multiply-Charged and Singularly-Charged Borane and Carborane Salts (Two Structural Salt Examples):

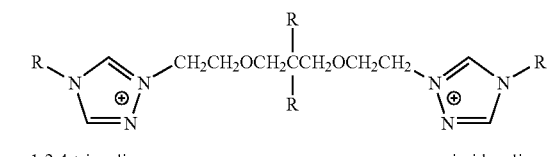

1,2,4-triazolium cation      imidazolium cation

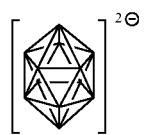

$B_{12}H_{12}^{2-}$

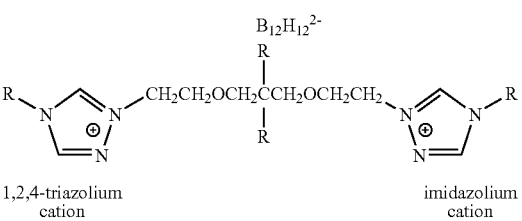

1,2,4-triazolium cation      imidazolium cation

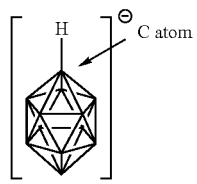 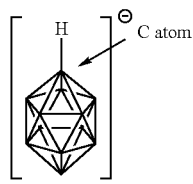

$CB_{11}H_{12}^{-}$      $CB_{11}H_{12}^{-}$

G. Heterocyclic Cations with Energetic Pendant Groups for Borane and Carborane Salts (Eight Structural Salt Examples):

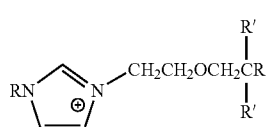

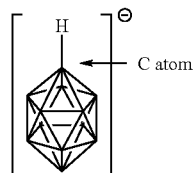

$CB_{11}H_{12}^{-}$

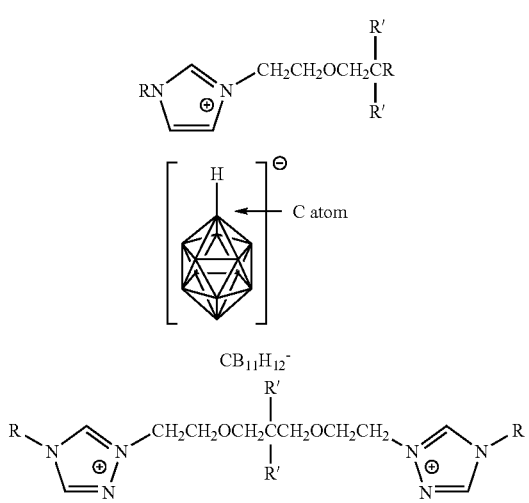

$B_{12}H_{12}^{2-}$

-continued

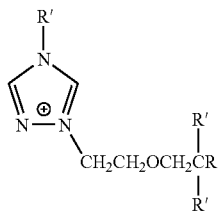

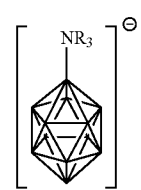

$R_3NB_{12}H_{11}^{-}$

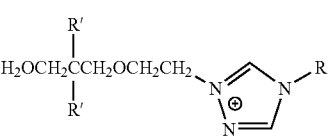

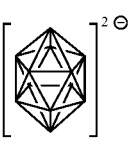

$B_{12}H_{12}^{2-}$

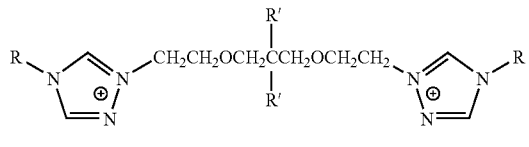

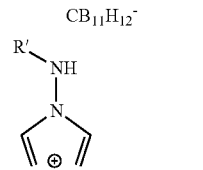 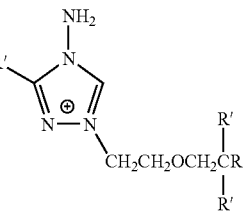

$CB_{11}H_{12}^{-}$      $CB_{11}H_{12}^{-}$

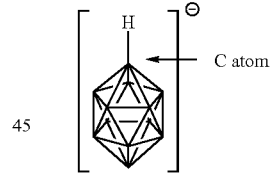 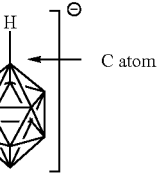

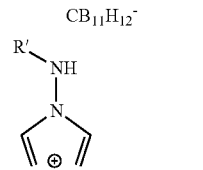 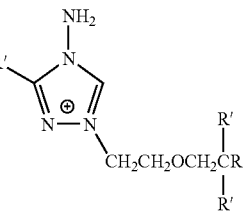

$CB_{11}H_{12}^{-}$      $CB_{11}H_{12}^{-}$

-continued

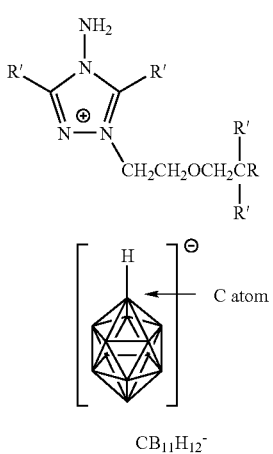

R' = Energetic Groups or Substituents

H. Multiply-Charged Heterocyclic Cations for Fluorinated Borane and Carborane Salts (Two Structural Salt Examples):

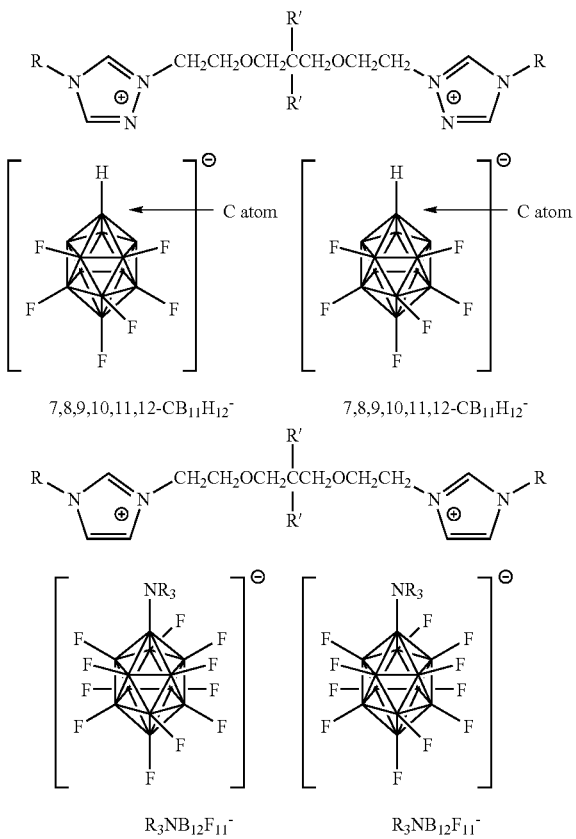

F-CONTAINING CARBORANE ANIONS = $CB_{11}H_{12}^{\ominus}$; $12\text{-}CB_{11}H_{11}F_1^{\ominus}$; $7,12\text{-}CB_{11}H_{10}F_2^{\ominus}$; (no F-atoms) $7,8,10,12\text{-}CB_{11}H_8F_4^{\ominus}$; $7,8,9,10,12\text{-}CB_{11}H_6F_6^{\ominus}$; and $CB_{11}HF_{11}^{\ominus}$ F-CONTAINING BORANE ANION = $R_3NB12F_{11}^{\ominus}$ These new materials will provide a unique new type of fuel with a non-existent vapor pressure and a significant density increase over previously used propellants ingredients. The low vapor pressure provides a substantial health hazards advantage from accidental inhalation, and the high density allows more energy to be packed into volume limited propulsion systems. The high density also will provide a higher density impulse which increases propellant energetic performance. The low molecular weights obtained from the combustion of these ingredients further should enhance propellant specific impulse performance to allow heavier missile payloads or increased range. The heterocyclic borane and carborane salts, that contain partially fluorinated borane and carborane anions in the proper stoichiometry, could improve the efficiency of boron and aluminum metal combustion in metallized propellant formulations and afford a higher specific impulse.

These new heterocyclic borane and carborane salts may also be modified for use as monopropellant ingredients by placing oxidizer-type pendant groups into the heterocyclic cation species, or could be used for gas generator and hydrogen storage applications.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. Salt compositions comprising heterocyclic borane salts (HBS) or heterocyclic carborane salts (HCS) or a combination thereof wherein one or more of the cations of salts are selected from the group below consisting of:

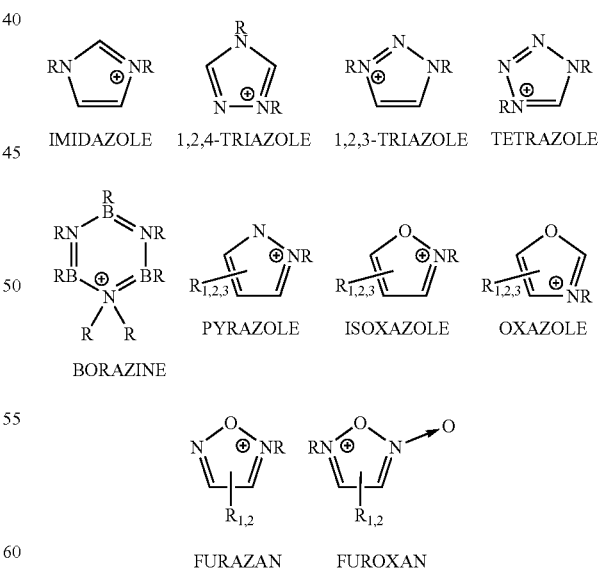

which cations are linked with an anion selected from the group consisting of $B_{12}H_{12}$, $R_3NB_{12}H_{11}$ and $CB_{11}H_{12}$ to form said salts for each of said cations, where R can be H, alkyl or amino as can $R_1$, $R_2$ and $R_3$.

2. The salts compositions of claim 1 wherein said HBS has the formula of

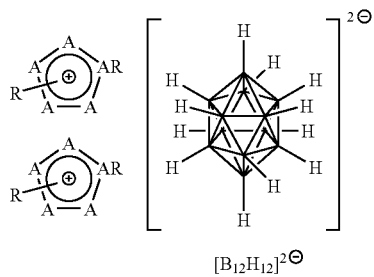

and said HCS has the formula of

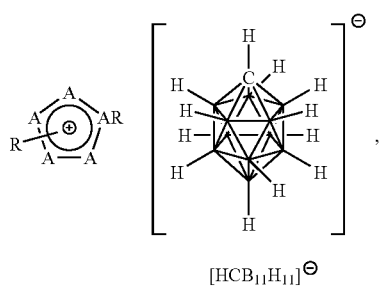

where A is C, N or O in the first ring position, A is C or N in the remaining ring positions and R is H, $NH_2$ or Alkyl.

3. The salts compositions of claim 1 comprising at least one of said cations and an anion of salts selected from the group consisting of

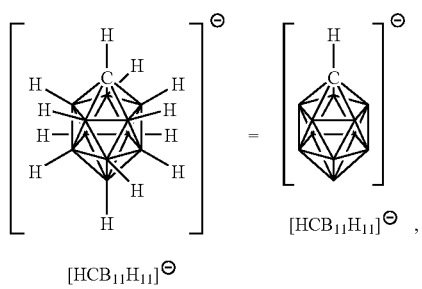

CARBORANE ANION
CLOSED ICOSAHEDRAL POLYHEDRON
WITH BORON ATOMS AT 11 CORNERS
AND A CARBON ATOM AT APEX

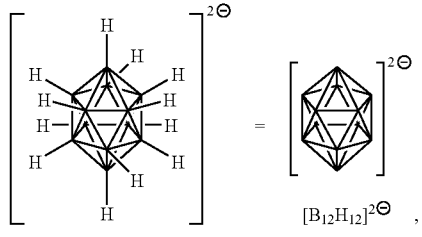

BORANE DI-ANION
CLOSED ICOSAHEDRAL POLYHEDRON
WITH BORON ATOMS AT ALL 12 CORNERS and

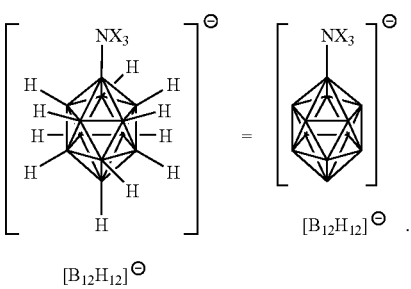

BORANE ANION
CLOSED ICOSAHEDRAL POLYHEDRON
WITH BORON ATOMS AT ALL 12 CORNERS

4. The salts compositions of claim 1 where said HBS is the following species:

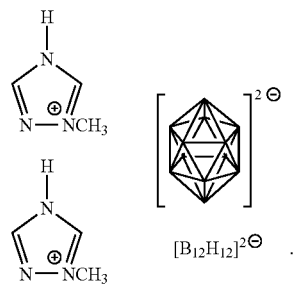

1,2,4-TRIAZOLE
CATION ISOMER

5. The salts compositions of claim 1 wherein said anions of salts have the following formulas:

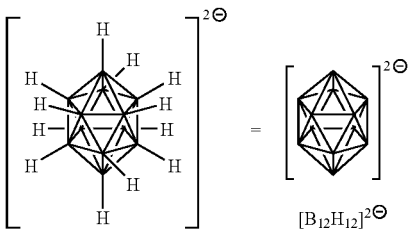

BORANE DI-ANION
CLOSED ICOSAHEDRAL POLYHEDRON
WITH BORON ATOMS AT ALL 12 CORNERS

-continued
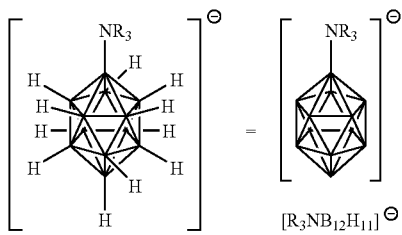 = 
$[R_3NB_{12}H_{11}]^{\ominus}$      $[R_3NB_{12}H_{11}]^{\ominus}$
BORANE ANION
CLOSED ICOSAHEDRAL POLYHEDRON
WITH BORON ATOMS AT ALL 12 CORNERS
R = H, Alkyl
-continued
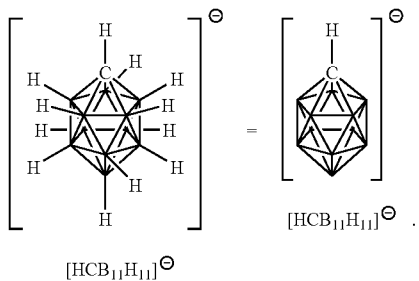 = 
$[HCB_{11}H_{11}]^{\ominus}$      $[HCB_{11}H_{11}]^{\ominus}$ .
CARBORANE ANION
CLOSED ICOSAHEDRAL POLYHEDRON
WITH BORON ATOMS AT 11 CORNERS
AND A CARBON ATOM AT APEX
\* \* \* \* \*